United States Patent [19]

Barrett

[11] Patent Number: 4,936,850
[45] Date of Patent: Jun. 26, 1990

[54] INTRAOCULAR LENS IMPLANT

[75] Inventor: Graham D. Barrett, City Beach, Australia

[73] Assignee: Ezekiel Nominees Pty. Ltd., West Perth, Australia

[21] Appl. No.: 330,991

[22] Filed: Mar. 29, 1989

Related U.S. Application Data

[63] Continuation of Ser. No. 824,833, Jan. 31, 1986, abandoned, which is a continuation-in-part of Ser. No. 640,098, Aug. 13, 1984, Pat. No. 4,664,666.

[30] Foreign Application Priority Data

Aug. 30, 1983 [AU] Australia .................................. 1120

[51] Int. Cl.$^5$ ............................................. A61F 2/16
[52] U.S. Cl. ............................................... 623/6
[58] Field of Search ................................... 623/6

[56] References Cited

U.S. PATENT DOCUMENTS

| | | | |
|---|---|---|---|
| 3,961,379 | 6/1976 | Highgate | 623/6 X |
| 4,073,015 | 2/1978 | Peyman | 623/6 |
| 4,113,088 | 9/1978 | Binkhorst | 623/6 X |
| 4,242,672 | 1/1981 | Tennant | 623/6 |
| 4,249,272 | 2/1981 | Poler | 623/6 |
| 4,254,509 | 3/1981 | Tennant | 623/6 |
| 4,254,510 | 3/1981 | Tennant | 623/6 |
| 4,257,521 | 3/1981 | Poler | 206/5.1 |
| 4,261,065 | 4/1981 | Tennant | 623/6 |
| 4,315,336 | 2/1982 | Poler | 623/6 |
| 4,402,579 | 9/1983 | Poler | 623/6 |
| 4,423,809 | 1/1984 | Mazzocco | 206/5.1 |
| 4,424,597 | 1/1984 | Schlegel | 623/6 |
| 4,449,257 | 5/1984 | Koeniger | 623/6 |
| 4,556,998 | 12/1985 | Siepser | 623/6 |
| 4,573,998 | 3/1986 | Mazzocco | 623/6 |
| 4,718,904 | 1/1988 | Thornton | 623/6 |

FOREIGN PATENT DOCUMENTS

| | | | |
|---|---|---|---|
| 2717706 | 10/1978 | Fed. Rep. of Germany | 623/6 |
| 1103399 | 5/1955 | France | 623/6 |
| 48-25748 | 7/1973 | Japan . | |
| 51-151149 | 12/1976 | Japan . | |
| 52-103488 | 8/1977 | Japan . | |
| 58-15142 | 3/1983 | Japan . | |
| 2114315A | 8/1983 | United Kingdom | 623/6 |
| 2151371A | 7/1985 | United Kingdom | 623/6 |

OTHER PUBLICATIONS

"The Soft Intraocular Implant", by K. R. Mehta et al., VI Congress of the European Society of Medicine, 1981, pp. 859–863.
"Ophthalmic Hydrogels", by Miguel F. Refojo, Technomic, Technomic Publishing Co., Inc., 1980, pp. 171–185.
Translation, Dreifus et al., Cs. oftamologie, vol. 16(2), pp. 454–459 (1960).
Mehta et al., "The New Soft Intraocular Lens Implant", AM IntraOcular Implant Soc. J., vol. IV, Oct. 1978, pp. 200–205.
Lens Styles from CILCO.
Ceskoslovenska, *Ofthalmologie*, 1960.

Primary Examiner—Ronald L. Frinks
Attorney, Agent, or Firm—Lowe, Price, LeBlanc, Becker & Shur

[57] ABSTRACT

A self-supporting intraocular lens formed entirely of a hydrogel and comprising a relatively thick central optic portion with relatively thin resilient flange portions.

22 Claims, 4 Drawing Sheets

INTRAOCULAR LENS IMPLANT

This application is a continuation of application Ser. No. 06/824,833, filed Jan. 31, 1986, now abandoned, which in turn is a continuation-in-part of application Ser. No. 06/640,098, filed Aug. 13, 1984, now U.S. Pat. No. 4,664,666.

FIELD OF THE INVENTION

This invention relates to improved intraocular lens implants, and more particularly to intraocular lens implants formed of a hydrogel.

BACKGROUND

Various types of intraocular lens implants are known to the art. Most of the known implants, however, are constructed of a rigid material and designed for physical attachment to the iris. For example, U.S. Pat. Nos. 4,242,762, 4,254,509 and 4,261,065 to Tennant disclose intraocular lens constructions for placement in the eye. The device in 4,242,762 for posterior chamber placement is provided with a triangular base element with an optic element positioned therein and a pin extending from one corner and secured in place by a combination of tissue scarring within the capsular sac and clipping of the lens to the iris with a platinum pin. The lens construction comprises a polymethylmethacrylate or pHEMA haptic portion and an optic portion of either polymethylmethacrylate or pHEMA, but there is no disclosure of a lens constructed entirely of pHEMA. In U.S. Pat. No. 4,254,509, anterior chamber eye implant is disclosed which comprises a dumbbell-shaped optical lens having an anterior convex surface and a posterior planar surface and supported on diametrically opposed coplanar feet through two supporting members which form an arch. The lens may be formed of a rigid material such as polymethylmethacrylate or soft materials of the hydrophilic type such as 2-hydroxyethylmethacrylate referred to as pHEMA. In the preferred construction, the lens section is composed of a hard material while the haptics or arches are made of soft material. This embodiment is preferred in this patent so that if the soft haptics portion is moved, the rigid lens section will not be distorted. The anterior chamber device in 4,261,065 is for positioning in the anterior chamber on the scleral spur. The lens is made of PMMA.

U.S. Pat. No. 3,961,379 to Highgate discloses bioimplantable devices in general produced from crosslinked swollen hydrophilic polymers with suggested uses as prosthetic devices. The polymers include alkyl and hydroxyalkyl acrylates and methacrylate polymers The polymers are modified by a swelling technique. No particular structures of prosthetic devices are disclosed.

U.S. Pat. Nos. 4,249,272, 4,257,521, 4,402,579 and 4,315,336 to Poler disclose intraocular lens structures to be used as implants in ophthalmological surgery and packaging means for intraocular lenses. The structures in 4,249,272 and 4,257,521 comprise a circular, optically finished lens element with a plurality of angularly spaced stabilizing feet formed integrally with the body of the structure. The device is designed to be placed within the posterior chamber The implant disclosed in No. 4,249,272 appears to comprise two sections wherein the central focussing body or lens is of one material and the haptic section is of a different material. There does not appear to be any disclosure that the entire lens could be an integral piece of a single material. The disclosure in 4,257,521 concerns a packaging device for implants of this type in general. The lenses are prepared from a plastic sheet as described in 4,402,579. Reference is made incorrectly to HEMA in columns 5 and 6 of 4,402,579 since the patentee is obviously referring to polymethylmethacrylate (PMMA). The device in 4,315,336 comprises a haptic element secured to a glass lens.

U.S. Pat. No. 4,449,257 discloses an intraocular lens of HEMA plastic in the form of a round lens with concentric grooves around the peripheral margins for frictional engagement with the rough interior walls of the posterior capsule. The lens is cut to a size that is small for implacement but softens and expands to fill a posterior chamber capsule after it has been emptied of its natural contents. The softening and expanding of the lens is caused by aqueous humor uptake into one of the dry lenses from the capsule environment. The concentric grooves frictionally engage the rough interior walls of the capsule to position and retain the lens in place.

In a review article by Refojo, published in Technomic, Technomic Publishing Company, Inc., 1980, pages 171-185, entitled "Ophthalmic Hydrogels", there is a discussion of ophthalmic hydrogels and their use in ophthalmology. This review article is a general discussion of the benefits and disadvantages of hydrogel materials in general for such devices as corneal contact lenses, corneal prosthesis and intraocular lens implants. The discussion with respect to intraocular lens implants suggests that polymethylmethacrylate is very well tolerated by eye tissues and that some models of lenses have supporting loops or flanges of different materials. The article also discusses glaucoma drainage devices, scleral buckling and retinal detachment surgery and vitreous implants.

In a publication by Wichterle, Ceks Oftalmol 16:154-159 (1960), there is disclosed in an English abstract the suggestion for use of tridimensional polymers with high water contents to obtain stability of shape in intracameral lenses. There is no specific discussion with regard to structure of such devices.

In two publications by Mehta et al, VIth Congress of the European Society of Ophthalmology, Royal Society of Medicine International Congress and Symposium Series No. 40, published jointly by the Academic Press Inc. (London) Ltd. and the Royal Society of Medicine, 1981, pages 859-863, and American Intra-Ocular Implant Society Journal, Vol. IV, October 1978, pages 200-205, there is publication of the considerable work by Mehta and associates in soft intraocular lens implants. These publications disclose the use of soft implant materials using the iris fixation technique with disclosure of various types of implants which have been tested, including a dumbbell-shaped optical lens and a series of other related structures. The publication in the American Intra-Ocular Implant Society Journal suggests that the choice of material for the implant is one which provides the highest degree of hydration consonent with a stable lens, the material must be machined or lathed easily, the material must be safely autoclaved repeatedly without distortion of lens parameters, should be able to withstand surgical handling and should not discolor or degrade in storage. A material identified as Soflex 44-R was selected as a preferred material. This Soflex 44-R is a commercial material comprising pHEMA. However, this publication suggests that a soft lens implant cannot be made self-supporting and a central support, i.e., iris fixation, must be used to ensure stability of the lens. Mehta et al. further suggest that this iris supported lens should be implanted following either extracapsular or intracapsular cataract extraction.

All of these Mehta et al prior art disclosures, however, are based on the concept of iris fixation in implacement in the eye and require difficult surgical techniques.

British Patent publication No. 2,114,315A, published Aug. 17, 1983 to Mazzocco discloses an intraocular lens which has a deformable optical zone with known memory characteristics. The thrust of this patent is that the entire lens is provided with memory characteristics so that the lens can be deformed, such as by compressing or rolling to 80% or less of the cross-sectional diameter of the optical zone in an unstressed state. The lens is made sufficiently thin so that it can be folded for insertion through small incisions. The patentee discloses that the optical zone portion can be made from a hydrogel polymer, but there is no enabling disclosure in the patent as to how the hydrogel polymer would be used to produce a structure of this type.

U.S. Pat. No. 4,424,597 to Schlagel discloses a posterior chamber implant lens which is provided with a central lens body and a holding means arranged on the lens body which extends radially outwards from the periphery of the body. The lens is made of a vulcanized silicone rubber.

In an advertisement brochure from Cilco, Inc. 1616 13th Avenue, Box 1680, Huntington, W.V. 25717, October, 1982, various styles of intraocular lenses are disclosed. The lenses are referred to as perspex CQ lenses. Perspex is a methylmethacrylate polymer.

U.S. Pat. Nos. 4,113,088 to Binkhorst and 4,423,809 to Mazzocco disclose packaging systems for intraocular lens structures.

None of the above mentioned prior publications, however, disclose novel intraocular lens implants which are self-supporting and are made entirely from a hydrogel.

SUMMARY OF THE INVENTION

It is accordingly one object of the present invention to provide a novel intraocular lens implant formed entirely of a hydrogel which is self-supporting, and causes minimal endothelial damage on contact with the corneal endothelium.

A further object of the invention is to provide an intraocular lens formed entirely of a hydrogel which is hydratable to become soft and flexible, of integral construction, and comprises a relatively fixed central or lens portion and a tapered flange portion as support means.

An even further object of the invention is to provide a self-supporting intraocular lens formed entirely of a hydrogel which is insertable in the posterior chamber of the eye and retained in position by engagement of the flange portion within the ciliary sulcus or capsular bag of the eye, said engagement being without suturing or other forms of mechanical affixation to the iris of the eye.

Other objects and advantages of the present invention will become apparent as the description thereof proceeds.

In satisfaction of the foregoing objects and advantages there is provided by this invention an intraocular lens suitable for use as an artificial lens in the interior of a human eye, said lens being formed entirely of a hydrogel and comprising a relatively thick central optical portion having a posterior face and an anterior face, and having a relatively thin, tapered, resilient flange portion extending away from said optical portion;

said lens maintaining its shape when in hydrated or dehydrated form and said optical portions being sufficiently thick and rigid to provide stable optical correction.

BRIEF DESCRIPTION OF THE DRAWINGS

Reference is now made to the drawings accompanying the application wherein.

DESCRIPTION OF PREFERRED EMBODIMENTS

It is known to replace the natural crystalline lens following cataract extraction. Many people on whom cataract operations are performed receive an intraocular lens implant. However, there is a need for a safer and more effective intraocular lens than those which have been available hitherto. The most commonly used material for intraocular lenses has been polymethylmethacrylate (PMMA). PMMA has a number of characteristics making it suitable for use as an intraocular lens implant. Silicone is another type of material frequently used in intraocular lenses. Both of these types of materials have been shown to be particularly injurious to the corneal endothelium. The corneal endothelium is a thin layer at the back of the cornea. The maintenance of corneal clarity is dependent on the endothelium which is essentially non-regenerative. There appears to be a biophysical interaction between the hydrophobic PMMA or silicone and the endothelium such that even a momentary touch on insertion will cause significant endothelial cell disruption by adherence of the cells to the lens surface.

Loss of endothelial cells at the time of surgery can lead to loss of corneal transparency several years later In addition, there are other problems attendant with the use of PMMA as an implant material.

The present invention provides a self-supporting intraocular lens to be implanted into the eye, the lens being formed entirely of a hydrogel. According to the present invention it has surprisingly been found that a self-supporting intraocular lens formed entirely of a hydrogel material overcomes problems with the prior art in this area. Thus, the hydrogel intraocular lens of this invention provides outstanding advantages in being soft and flexible and causing minimum endothelial damage even on extended contact with the corneal endothelium. The hydrophilic nature of the hydrogel lens of the invention provides outstanding advantages in endothelial tolerance as compared to prior art lenses. The lens is preferably of integral construction of a single hydrogel material; however, in a further embodiment, the lens may be made of two different types of hydrogel materials while still retaining the advantages of a hydrogel lens.

The lens structure according to the present invention is such as to provide an optical portion which is sufficiently thick and rigid to provide stable optical correction when inserted into the eye. It is a feature of the invention that the lens construction has a relatively thick, centrally located optical portion with a posterior face and an anterior face.

Figure 2:
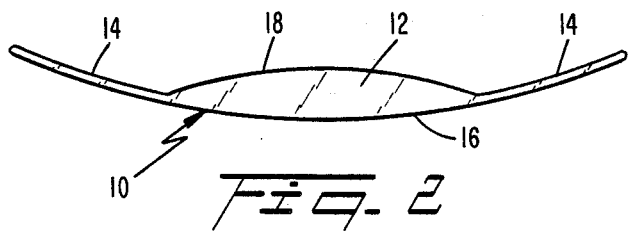
FIG. 2 is a side elevation of the intraocular lens implant of FIG. 1.
Figure 3A:
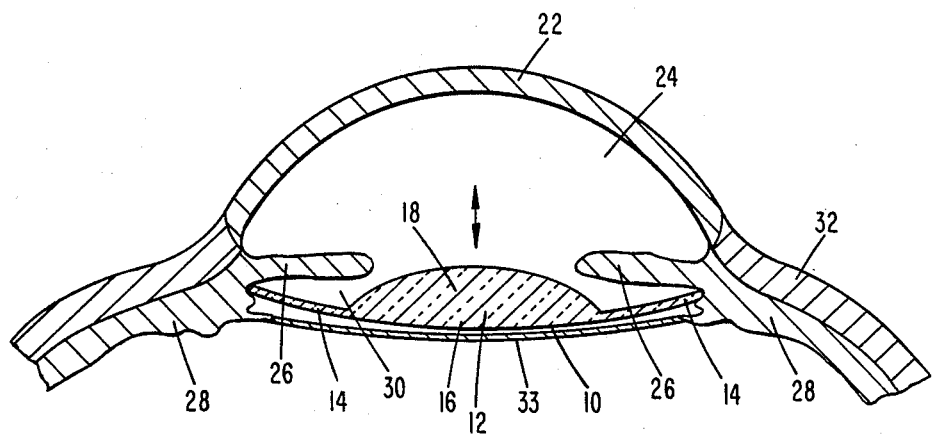
FIG. 3a is a cross-sectional view of an eye containing an implant, according to FIGS. 1 and 2 in place with a ciliary sulcus placement.
Figure 3B:
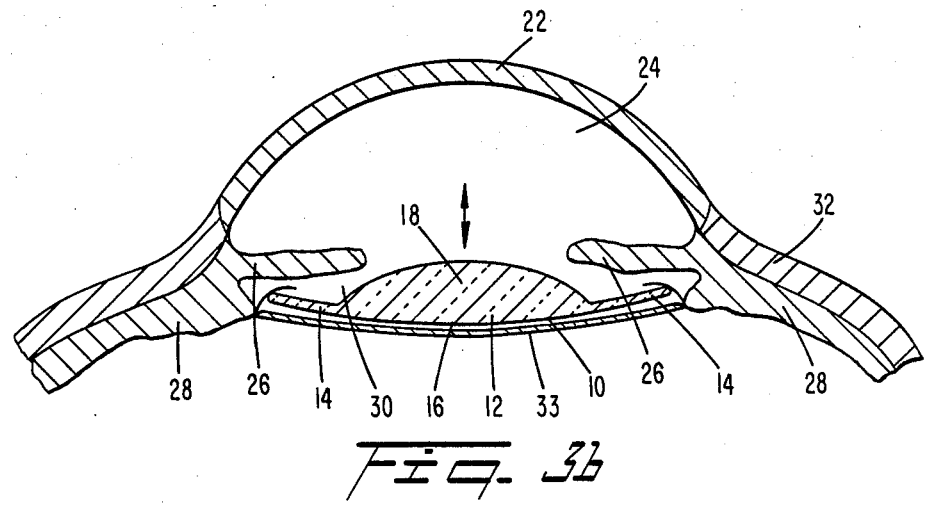
FIG. 3b is a cross-sectional view of an eye with an implant according to FIGS. 1 and 2 in place with a capsule bag placement.

In a preferred embodiment, the optical portion has an asymmetric, biconvex construction. The preferred ratio of curvature between the curvature of the posterior face and the curvature of the anterior face of the biconvex optical portion is on the order of 3:1. For purposes of the present specification, the term "ratio of curvature" is defined as the ratio of the radius of curvature of the posterior face to the radius of curvature of the anterior face. The radius of curvature may be determined by extending the arcs defining the posterior and anterior faces of the optical portion into circles and measuring the radius of each circle. Thus, a lens having the preferred ratio of curvature of about 3:1 will have a posterior face curvature which is relatively flat compared to the curvature of the anterior face of the optical portion; a lens of this type is illustrated in FIGS. 2, 3a and 3b. This preferred ratio of curvature has been found to provide the lens with optimum optical properties Further background regarding the importance of certain ratios of curvature in intraocular lenses is provided in the following article: Wang et al, "Obtaining a High-Quality Retinal Image with a Biconvex Intraocular Lens", *American Journal of Ophthalmology*, vol. 94, pages 87-90 (1982).

It is a further feature of the invention that there is present at least one relatively thin, resilient, flange portion extending laterally away from said optical portion which supports the lens and enables the lens to remain in position in the eye. The flange portion may be of various forms as set forth herein in separate embodiments.

For example, the flange portion may have a substantially circular or triangular configuration when viewed from the front or rear of the lens, in which cases the flange portion surrounds the lateral periphery of optical portion in an annular fashion; or may comprise two or more laterally extending appendages of various shapes located at the periphery of the optical portion.

The flange portion projects away from the vertical plane of the optical portion toward the iris of the eye so that the optical portion is disposed away from the iris. Such flange portions thus project posteriorly in anterior chamber lenses and anteriorly in posterior chamber lenses. These flange portions are preferably curved. The above-described flange portion design is very important, because it allows the lens to move slightly along the visual axis of the eye when radial compressive forces are applied to the flange portion. This ability prevents the lens from being displaced from alignment with the visual axis upon compression of the flange portion, thereby maintaining visual acuity. Such displacement is a significant problem with prior art single piece, soft lenses having soft flanges which are substantially in the same plane as the optical portion. Lens displacement has particularly been a problem with prior art posterior chamber lenses of this type, as discussed in greater detail below.

A very important feature of the posterior chamber lenses of the present invention is that the lenses have structures which allow for predictable displacement along the visual axis when the flanges of the lenses are compressed. The capsular bag, more particularly the portion of the capsular bag remaining after removal of the natural crystalline lens (i.e., the "posterior capsule"), normally contracts post-surgically. If the lens is implanted in the capsular bag, this contraction exerts compressive forces directly on the haptic or flange portion of the lens. Displacement of the lens from the capsular bag is a problem which has been experienced with prior art single piece, soft lenses having soft flanges which are substantially in the same plane as the optical portion of the lens (i.e., flanges which do not project or curve anteriorly). This is generally not a problem with a lens having looped haptics, since the loops may be compressed in the plane of the lens without causing the lens to be displaced from the capsular bag. However, lens displacement is a very significant problem with prior art single piece, soft lenses having soft flanges, since contraction of the capsular bag frequently causes such prior art lenses to buckle or pivot, so that all or part of the lens is displaced from the capsular bag. As a result of this displacement, the lens is frequently no longer in alignment with the visual axis of the eye; this misalignment of the lens will normally result in visual disturbances and decreased visual acuity, if not total loss of visual accuity. This misalignment must then be corrected by a further surgical procedure where the lens is reimplanted in the ciliary sulcus (replacement of the lens in the capsular bag is either impossible or extremely difficult at this point due to the contraction of the capsular bag).

The posterior chamber lenses of the present invention have been specifically designed to avoid this problem. As mentioned above, the posterior chamber lenses of the present invention have flanges which project anteriorly. This flange structure has been found to provide for predictable displacement of the lens along the visual axis, generally posteriorly along the visual axis. That is, when the anteriorly projecting flanges are compressed by the contracting capsular bag, the flanges flex rather than pivoting or buckling, whereby the lens merely moves slightly along the visual axis of the eye instead of being displaced from the capsular bag. This feature of the present invention is believed to represent a very significant improvement over the prior art.

The above-discussed ability of the posterior chamber lenses of this invention to move in the direction of the optical axis when the flanges thereof are compressed also enables the lenses to be used in a greater variety of eye sizes. The diameters of the ciliary sulcus and capsular bag vary from patient to patient. In order for a posterior chamber lens to fit properly in the eye, its diameter must be equal to or slightly greater than the diameter of either the ciliary sulcus or capsular bag, depending on where it is implanted. If the diameter of the lens is less than the diameter of the ciliary sulcus or capsular bag, the lens cannot be properly supported or positioned in the eye. It has generally not been possible or advisable to implant prior art soft, single piece lenses having flanges in the same plane as the optical portion of the lens rather than loops and having diameters significantly greater than the diameters of the ciliary sulcus or capsular bag, because of buckling and displacement of such lenses upon compression of the flanges during or subsequent to implantation. The posterior chamber lenses of the present invention are capable of being inserted in eyes having ciliary sulcus or capsular bag diameters significantly smaller (i.e., about 1 mm smaller) than the diameter of the lens, because the flanges of the lens can be readily compressed, thereby effectively decreasing the diameter of the lens, without buckling or causing displacement of the lens. Thus, the posterior chamber lenses of the present invention are more versatile with regard to obtaining a proper fitting of the lenses in the eye compared to soft, single piece, lenses of the prior art having soft flanges in the same plane as the optical portion of the lens.

It should be further noted that the diameter of the ciliary sulcus and capsular bag may be different in a particular patient; more particularly, the diameter of a patient's capsular bag is frequently less than the diameter of the patient's ciliary sulcus. In such cases, the above-described feature of the invention allows a lens having a diameter compatible with the ciliary sulcus to also be inserted in the capsular bag. This is a further illustration of the versatility of the present lenses.

It is a further feature of the invention that the lens is "self-supporting". By the term "self-supporting" it is meant that unlike prior art lenses such as those discussed above, the lenses of the present invention do not require fixation to the iris to remain in position after insertion into the eye. Rather, the lenses of the invention are designed to be retained in position in the eye by engagement of at least one flange portion within the ciliary sulcus or capsular bag of the eye.

A still further feature of the present invention is seen in certain particularly preferred embodiments of the posterior chamber lenses according to the invention. In these embodiments, the lens has a continuous, convex surface posteriorly. That is, the posterior surface of the lens is a continuous, convex curve extending from the tip of one flange across the optical portion of the lens to the tip of a second flange on the opposite side of the lens. (This type of lens is illustrated in FIGS. 2, 3a and 3b, and is described in greater detail below). The continuously curved, convex posterior surface of these lenses serves a very important function. Namely, the curvature of the lens surface is such that the posterior capsule will conform to the contour of the lens, thereby maximizing the contact between the posterior surface of the lens and the posterior capsule. This contact tends to smooth out any folds present in the posterior capsule. In addition, the contact between the lens surface and the posterior capsule achieves an optimum barrier effect which inhibits cellular proliferation along the anterior surface of the posterior capsule. It has been found that this inhibition is of significant assistance in preventing the formation of posterior capsule opacifications post-surgically.

As pointed out above, the lens is formed of a single hydrogel as an integral construction. Alternatively, in certain embodiments, the lens may be formed of two separate hydrogel materials, the lens portion being formed of one hydrogel material and the flange portion being formed of a different hydrogel material.

A hydrogel is an organic polymeric or copolymeric material comprising hydrophilic monomers. The hydrogel mixture swells upon being hydrated and becomes soft and flexible. One particularly useful hydrogel is hydroxyethyl methacrylate (HEMA) and it has been found that this material causes little endothelial damage on contact. Also, since hydrogels are hydrophilic in nature, endothelial damage is generally less than with PMMA or silicone. Other types of hydrogels which may be used in the present invention are copolymers of vinyl pyrrolidone with HEMA or methyl methacrylate, copolymers of glyceryl methacrylate and methyl methacrylate and copolymers of HEMA and diacetone acrylamide. It has been found in particular that a HEMA hydrogel lens manufactured from HEMA having the capability of absorbing about 38% of its weight of water, makes a particularly useful posterior chamber intraocular lens.

Preferably, the intraocular lens implant is of integral construction and comprises a relatively thick optical portion having relatively thin tapered resilient flange means extending away from it, said flange means being arranged to retain the implant in the eye.

Figure 1:
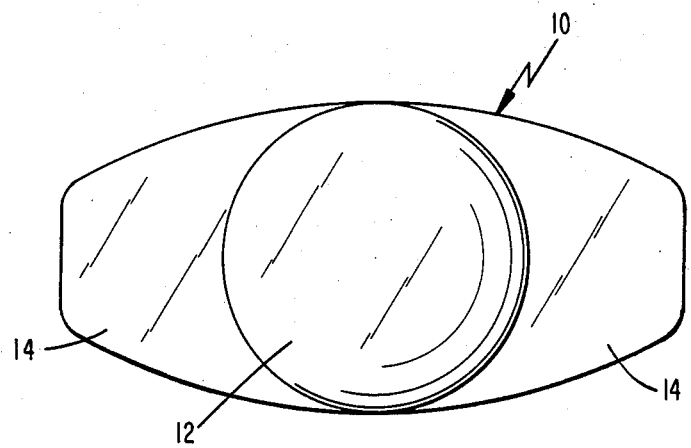
FIG. 1 is a plan view of a self supporting intraocular lens in accordance with one embodiment of the present invention.

Referring now to the drawings in detail, in FIGS. 1 and 2, there is shown a self-supporting intraocular lens 10 comprising a central optical portion 12 which is in the form of a lens. As shown, the lens construction does not rely on iris-fixation for support. The central optical portion 12 is flanked by laterally extending flanges 14. The implant has a posterior face 16 and an anterior face 18. The lens implant of FIGS. 1 and 2 is arranged to be inserted in the posterior chamber of an eye.

As can be seen in FIG. 2, the optical portion 12 is of asymmetrical bioconvex construction which gives good optical resolution. The posterior face 16 is at a standard curvature such as a curve having a radius of about 17 to 21 mm when unhydrated and about 21 to 25 mm when hydrated. The posterior face 16 is, in this case, a non-variable optical surface whilst the anterior face 18 is an optical surface of varying power. As may be seen from the profile of the lens in FIG. 2, the combination of the posterior face 16 with the flange portions 14, presents a continuous, curved surface. In other lens constructions, the anterior face 18 may be a non-variable optical surface of varying power. Thus, in the embodiment illustrated in FIG. 2, the optical properties of the optical portion 12 can be varied by varying the curvature of the anterior face of the optical portion 12. The ratio of curvature of the lens is approximately 3:1. Computer analysis has shown that this ratio provides optimum ocular resolution for an intraocular lens of this type. The power of each eye is different and therefore the thickness of the optical portion 12 and the curvature of the anterior face 18 thereof will vary from case to case. The techniques for forming the correct shape of the anterior face and thickness of the optical portion 12 are known.

In a preferred embodiment, the optical portion 12 and flanges 14 are formed in an integral unit, that is, the entire implant 10 is formed in one piece The flanges 14 may be of a wide variety of thickness but are preferably between 0.02 and 0.2 mm thick More preferably, the flanges 14 are between 0.10 and 0.18 mm thick such as about 0.14 mm thick. The optical portion 12 is thicker than the flanges 14 but, as described above, actual thickness of the optical portion will vary with optical requirements of the lens implant 10. A typical thickness for the optical portion 12 is about 0.9 mm.

The implant 10 is formed of a hydrogel material such as HEMA and the flanges 14 are therefore resilient. However, the optical portion 12 is thick enough to be sufficiently rigid to provide stable optical correction.

As can be seen in FIG. 2, the flanges 14 have a similar curvature to the posterior face 16. Thus the flanges 14 project anteriorly and, as will be described, dispose the implant 10 away from the iris in use. Further, the flanges 14 may be transversely tapered as can be seen in FIG. 1. This enables the flanges 14 to be inserted through a small pupil. The flanges 14 may, for example, taper from 6 mm at the optical zone 12 to 2 mm at their outer extremities.

The lens implant 10 can be manufactured by any suitable technique such as by forming a blank on a lathe, polishing the lens implant, checking the thicknesses of the various parts of the lens implant, checking in the dry state for any flaws, cleaning to remove residual wax or polish and then bathing the implant in saline solution. The hydrated implant can then be washed in a Soxhlet system and again examined for defects in the hydrated state. Other suitable manufacturing techniques include moulding or pressing to form a lens implant in accordance with the present invention. The power of the lens is measured in the hydrated state. The lens dimensions are thus measured in the hydrated state. Finally, the lens implant is placed in a sealed vial in a physiologically acceptable solution, such as a balanced electrolyte solution, saline, or distilled water and autoclaved to sterilize it. The electrolyte solution is preferably a balanced or isotonic salt solution which will hydrate the lens implant 10 and be compatible with the human eye. The vial is preferably a glass vial.

In FIG. 3a there is shown an eye comprising a cornea 22 which has an endothelium layer on its inner face. Behind the cornea there is an anterior chamber 24 which is filled with aqueous fluid. At the rear of the chamber 24 there is located the iris 26 which is in two parts separated by a gap which constitutes the pupil of the eye. At its outer edge the iris 26 is connected to ciliary sulcus 28. The region behind the iris 26 forms a posterior chamber 30 which also contains aqueous fluid. To the front of the ciliary sulcus 28 is the white 32 of the eye. To the rear of the posterior chamber is the posterior capsule 33 of the eye. As can be seen in FIG. 3a the lens implant 10 of FIGS. 1 and 2 is mounted in the eye in the posterior chamber 30. The lens implant 10 is retained in place by engagement of the flanges 14 in the ciliary sulcus 28.

There are two preferred methods of fixation for a posterior chamber lens in accordance with the present invention. The first method is illustrated in FIG. 3a in which the lens is fixed in place by engagement with the ciliary sulcus 28 and in this case the lens width may be from about 12 to 14 mm such as about 12.5 mm.

The second means of fixation is illustrated in FIG. 3b and is by means of the capsular bag of the eye. In this case the capsular bag fixes the lens in place. A lens intended for capsular bag placement would typically have a diameter in the range from about 10 to 12 mm, such as about 11 mm. In other respects the lens of FIG. 3b is similar to that of FIG. 3a.

FIGS. 3a and 3b illustrate important advantages of the lenses of the invention in mounting within the ciliary sulcus or capsular bag. In both cases, the curved anteriorly projecting lens, combined with the flanges contained within the ciliary sulcus or capsular bag prevent the lens from moving in a radial or sidewise manner and becoming displaced. Rather, when the lens attempts movement while in place, the flange portions are compressed and as a result flex against the ciliary sulcus or capsular bag and prevent sideways movement.

The flexing action of the flanges, combined with the self-supporting nature of the lens, causes movement to be substantially only posteriorly along the visual axis, as shown by the arrows in FIGS. 3a and 3b. Thus, the structure of the lens enables it to remain in position without iris fixation.

Figure 4:
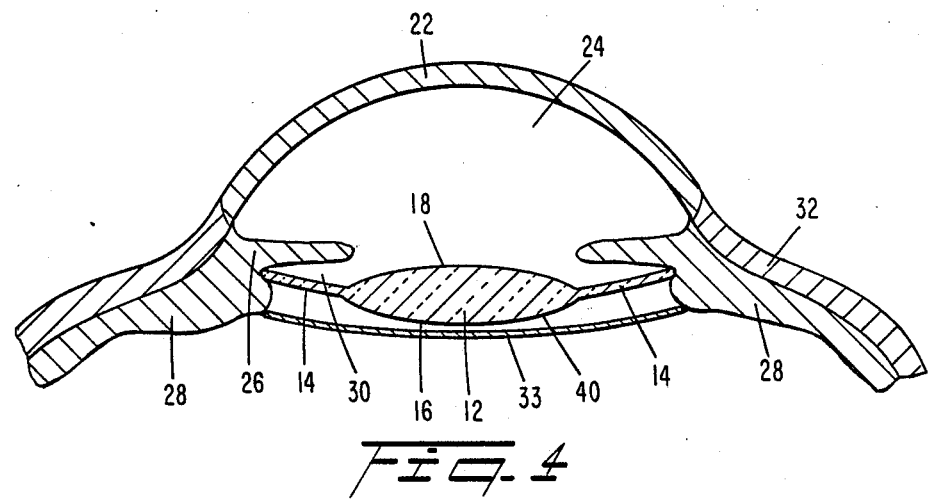
FIGS. 4, 5, 6 and 7 are views similar to that of FIG. 3a showing alternative intraocular lens configurations in accordance with the present invention.
Figure 5:
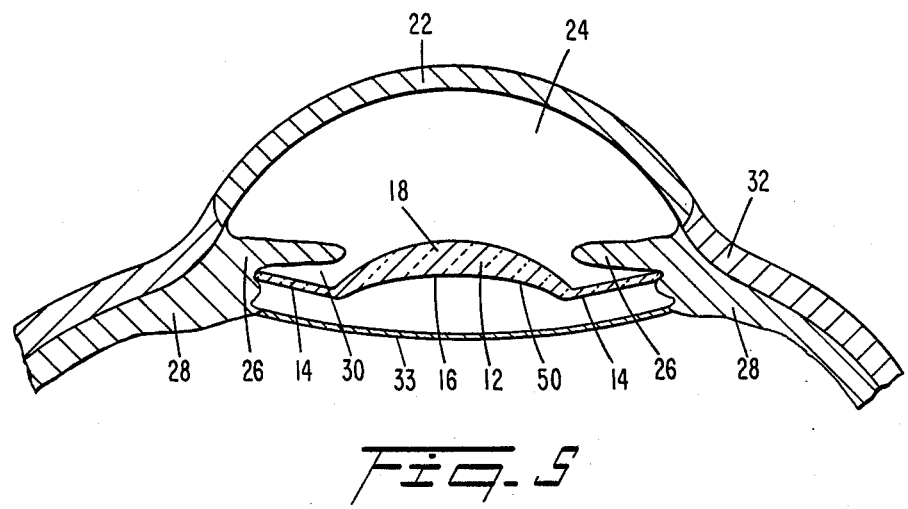
Figure 6:
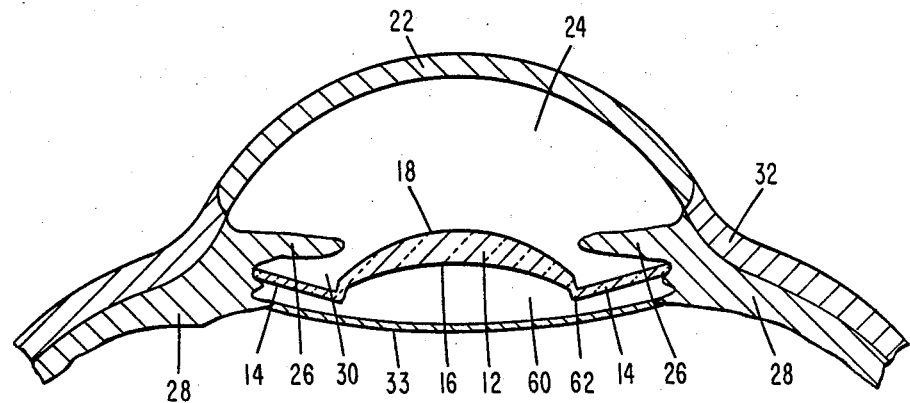

The intraocular lens implant of the present invention can take other forms as described herein. Thus FIGS. 4 to 9 illustrate various modifications of the lens implant shown in FIGS. 1 to 3 and like reference numerals denote like parts. The lens implants of FIGS. 4, 5 and 6 are intended for posterior chamber placement by engagement with the ciliary sulcus, but equivalent lenses can be made which are intended for capsule bag placement as shown in FIG. 3b.

An alternative form of intraocular lens implant 40 according to the present invention, intended for implantation in the posterior chamber of the eye, is shown in FIG. 4. In this case, the posterior face 16 is not of uniform curvature throughout but has increased curvature in the optical portion 12. The lens 40 is still of asymmetrical bioconvex construction.

An alternative form of intraocular lens implant 50 according to the present invention intended for implantation in the posterior chamber of the eye is shown in FIG. 5. In this case, the posterior face 16 has reverse curvature in the optical portion 12 and the lens 50 is of convex-concave construction. This construction is particularly effective for laser surgical techniques since the back of the lens structure provides a protuberance or ridge which can cover lens bag for laser surgery to remove small protuberances which may grow after lens surgery.

An alternative form of intraocular lens implant 60 according to the present invention intended for implantation in the posterior chamber of the eye is shown in FIG. 6. In this case, the optical portion of the posterior face 16 is located forwardly of the remainder of the posterior face 16 by means of a peripheral lip 62. The lens 60 is of asymmetrical biconvex construction.

Figure 7:
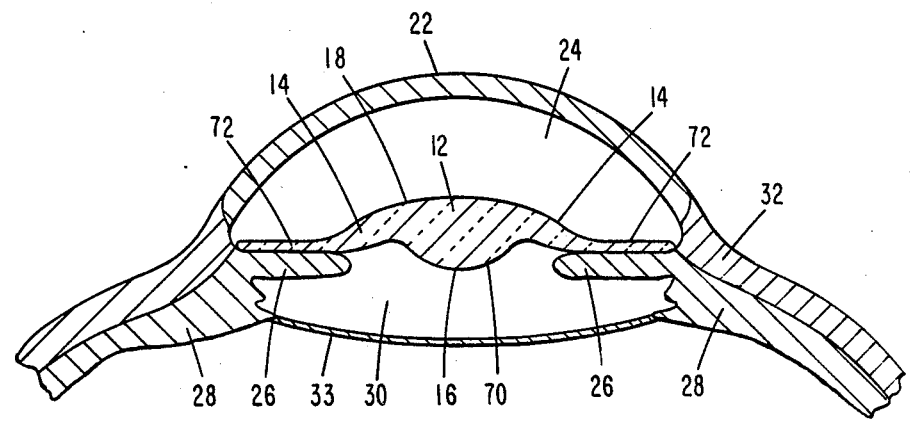
Figure 8:
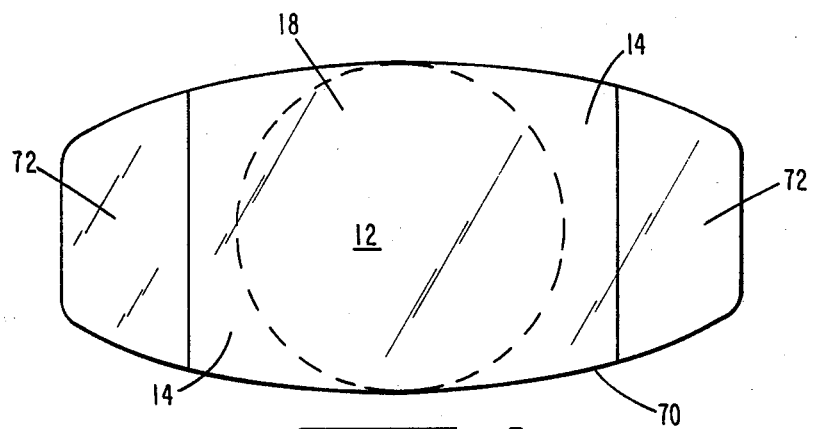
FIGS. 8, and 9 are plan and side views of other embodiments of the lens shown in FIGS. 1 and 2, respectively.

An alternative form of intraocular lens implant 70 according to the present invention intended for implantation in the anterior chamber of the eye is shown in FIGS. 7 and 8. In this case, the flanges 14 are provided with outwardly projecting feet 72 arranged to engage with the scleral spur or angle of the eye. The anterior face 18 of the implant 70 is of uniform convex curvature through the optical portion 12 and the flanges 14. The posterior face 16 also has a convex curvature so that the lens 70 is of asymmetrical biconvex construction.

Figure 9:
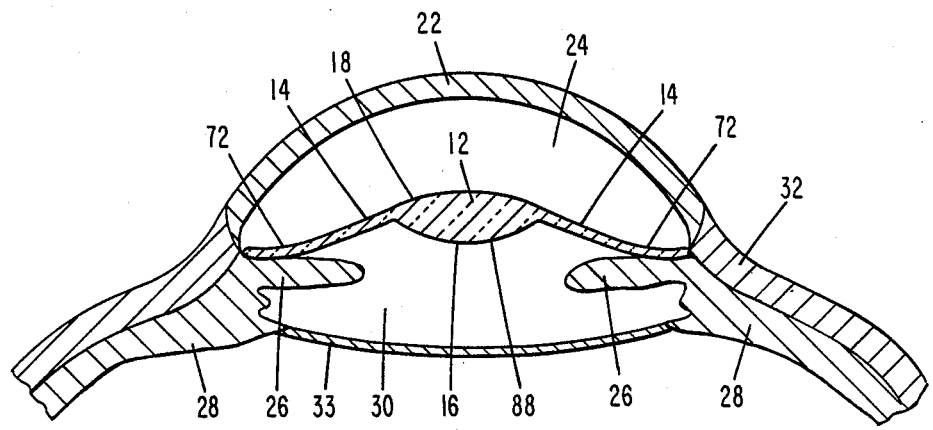

An alternative form of intraocular lens implant 88 according to the present invention intended for implantation in the anterior chamber of the eye is shown in FIG. 9. The lens of FIG. 9 is similar to that shown in FIGS. 7 and 8 and it also comprises the outwardly projecting feet 72. However, the anterior face 18 of the lens is of increased curvature in the optical portion 12 compared to the remainder of the anterior face 18.

Figure 10:
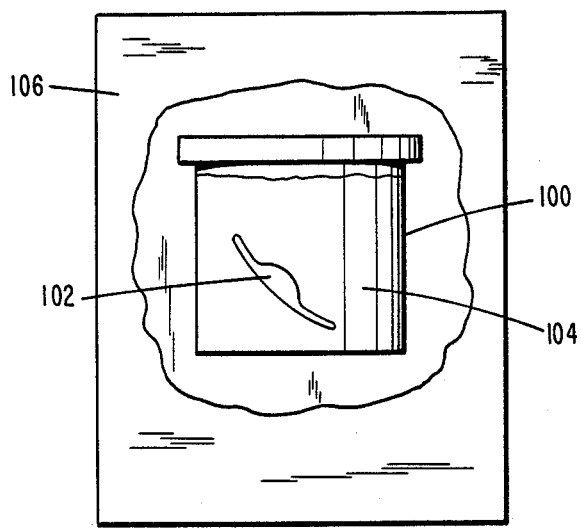
FIG. 10 is a side elevation of a package containing an intraocular lens implant in accordance with the present invention.

Preferably, a manufactured lens is washed a number of times in double distilled water to remove impurities from it and then autoclaved as described above. The autoclaving may be conducted for 15 to 30 minutes at a pressure in the range from about 120 to 130 mm mercury in a sealed vial containing a physiologically acceptable electrolyte solution. Then the sterilized vial is placed inside an internally sterile overpouch which is sealed and the autoclaving process is then repeated to ensure complete sterility of the completed product. A typical package comprising a sealed vial 100 containing a lens implant 102 and a quantity of physiologically acceptable saline solution 104 all contained within a flexible overpouch 106 is shown in FIG. 10.

The diameter of the optical portion 12 of a lens implant in accordance with the present invention is preferably from 3 to 10 mm, more preferably from 4 to 7 mm. The overall length of the lens implant may be from 8 to 15 mm. The non-variable optical surface of the optical portion 12 preferably ranges from plano to 10mm in radius of curvature, preferably from 15 to 30 mm radius of curvature. As stated above the radius of curvature of the optical surface of varying power is varied to adjust the optical power of the lens implant.

The lens implant of the present invention is particularly envisaged for use where a cataract has been removed. However, the lens implant of the present invention may be used to correct refractive errors and myopia without prior cataract extract. Thus, the lens implants of the present invention usually range from plano-convex to biconvex but as shown in FIG. 5, the posterior and anterior face of the optical portion 12 may have curves facing in the same direction which results in a concave-convex lens.

The lens implant of the present invention may include location members such as indentations, recesses or holes to assist in positioning the lens in the middle of the eye. The lens implant can be inserted at the time of cataract extraction or as a secondary implant. The lens can be inserted by the standard procedure.

Whilst it is preferred to insert the lens in hydrated condition from a vial as shown in FIG. 10, the lens implant could be inserted into the eye dry and hydrated subsequently to hydrate and swell it. The advantage of dry insertion is that it allows the lens implant to be inserted through a small wound in the eye.

The lens implant of the present invention may have a built in U.V. filter which is incorporated in the hydrogel. The U.V. filter can be incorporated in the chemical mix as polymerization takes place or a U.V. absorbing function can be built into the polymeric chain.

In a further embodiment of the invention the hydrogel plastic material from which the lens is constructed may be loaded with an ophthalmic medicinal material such as an antibiotic or the like. The ophthalmic medicinal material may be incorporated into the chemical mix as polymerization occurs and would then be contained within the finished lens. The ophthalmic chemical would then be released by the lens in the eye over a period of time to provide the ophthalmic medicinal material as required by the patient.

It is also envisaged that in some cases anterior chamber lens would be incorporated into a posterior chamber of the eye by being reversed.

Modifications and variations such as would be apparent to a skilled addressee are deemed within the scope of the present invention.

I claim:

1. A self-supporting, soft intraocular lens suitable for implantation in the posterior chamber of the human eye to replace the natural crystalline lens, comprising:

an optical portion having an anterior surface and a posterior surface, said optical portion being sufficiently thick and rigid to provide stable optical correction; and a pair of laterally extending flanges projecting from opposite sides of the optical portion, each flange having an anterior surface and a posterior surface, said flanges projecting anteriorly in the posterior chamber of the eye to dispose the optical portion away from the iris when the lens is implanted in the eye; said flanges functioning to support and retain the lens in place in the eye following implantation without fixation to the iris of the eye and having sufficient strength and flexibility so that the implanted lens can move slightly along the visual axis of the eye when forces are applied to said flanges so as to prevent said lens from being displaced from alignment with the visual axis, wherein said lens is formed entirely of a hydrogel and maintains its shape when in hydrated or dehydrated form.

2. An intraocular lens according to claim 1, wherein the flanges are imperforate.

3. An intraocular lens according to claim 1, wherein the hydrogel is hydroxyethyl methacrylate.

4. An intraocular lens according to claim 1, which is of integral construction.

5. An intraocular lens according to claim 1, wherein the posterior surface of the optical portion is convex and the flange means and posterior surface of the optical portion define a single, continuous arc.

6. An intraocular lens according to claim 1, wherein the flanges have a curvature in the range from plano to 10 mm radius.

7. An intraocular lens according to claim 6, wherein the optical portion of the lens is of asymmetrical bi-convex construction.

8. An intraocular lens according to claim 6 wherein the optical portion has a diameter of from 3 to 10 mm.

9. An intraocular lens according to claim 8 which has a length of from 8 to 15 mm in a horizontal direction across the eye.

10. An intraocular lens according to claim 1, wherein the optical portion has a non-variable optical surface having a curvature from plano to 10 mm radius.

11. An intraocular lens according to claim 1, wherein the optical portion has a non-variable optical surface having a curvature from 15 to 30 mm radius.

12. An intraocular lens according to claim 1, which is in hydrated form.

13. An intraocular lens according to claim 1, which is in hydrated form and is contained in a sealed vial containing a quantity of physiologically acceptable solution.

14. An intraocular lens implant according to claim 13, wherein the sealed vial is contained in a sealed overpouch.

15. An intraocular lens according to claim 1, wherein the hydrogel contains ophthalmic medication for release into the eye.

16. An intraocular lens according to claim 1, wherein the optical portion of the lens is of asymmetrical biconvex construction.

17. An intraocular lens according to claim 16 wherein the ratio of curvature between the curvature of the posterior face and the curvature of the anterior face is on the order of 3:1.

18. An intraocular lens according to claim 1, wherein the flanges flex when compressive forces are applied thereto and the lens resultantly moves slightly along the visual axis of the eye, whereby displacement of the flanges from the ciliary sulcus or capsular bag of the eye is substantially prevented and alignment of the optical portion with the visual axis of the eye is substantially maintained.

19. An intraocular lens according to claim 18 wherein the curvature of the lens surface is such that the posterior capsule substantially conforms to the contour of the lens thereby maximizing the contact between the posterior surface of the lens and the posterior capsule.

20. An intraocular lens according to claim 1, wherein the laterally extending flanges taper away from the optical portion so that the outer ends thereof are narrower than the optical portion.

21. An intraocular lens according to claim 20 wherein the curvature of the posterior surface of the lens is such that the posterior capsule substantially conforms to the contour of the lens thereby maximizing the contact between the posterior surface of the lens and the posterior capsule.

22. An intraocular lens according to claim 21 wherein the hydrogel is hydroxyethyl methacrylate.

* * * * *